United States Patent

Zybin et al.

Patent Number: 5,640,245
Date of Patent: Jun. 17, 1997

[54] SPECTROSCOPIC METHOD WITH DOUBLE MODULATION

[75] Inventors: Alexandre Zybin, Region Moskau, Russian Federation; Christoph Schnürer-Patschan, München; Kay Niemax, Stuttgart, both of Germany

[73] Assignee: LaserSpec Analytik GmbH, München, Germany

[21] Appl. No.: 448,633

[22] Filed: May 23, 1995

[30] Foreign Application Priority Data

Jun. 1, 1994 [EP] European Pat. Off. ............ 94108465

[51] Int. Cl.$^6$ ....................................... G01N 21/00
[52] U.S. Cl. ............................. 356/437; 356/432
[58] Field of Search .................... 250/343; 356/437, 356/432

[56] References Cited

U.S. PATENT DOCUMENTS

| | | | |
|---|---|---|---|
| 4,934,816 | 6/1990 | Silver et al. | 356/437 |
| 5,267,019 | 11/1993 | Whittaker et al. | 356/437 |

OTHER PUBLICATIONS

Journal of the Optical Society of America vol. 6, No. 5, May 1989 pp. 871–876; "High-sensitivity frequency-modulation spectroscopy with a GaAlAs diode laser"; Liang-Guo Wang, et al.

Journal of Physics D: Applied Physic's 26 (1993) 14 Feb., No. 2, Bristol, G.B. pp. 199–202; "Measurement of the CF3 radical using infrared diode laser absorption spectroscopy"; Kouji Maruyama, et al.

Applied Spectroscopy vol. 47, No. 3, 1993 Mar.; "Direct determination of trace elements in graphite matrices using modulated glow discharge atomic absorption spectrometry"; pp. 300–304;Ghangkang Pan, et al.

Analytical Chemistry, vol. 61, No. 21, Nov. 1, 1989 pp. 1217–1223; "Finding a single molecule in a haystack Optical detection and spectroscopy of single absorbers in solids"; W.E. Moerner, et al.

Primary Examiner—Frank G. Font
Assistant Examiner—Amanda Merlino
Attorney, Agent, or Firm—Nields & Lemack

[57] ABSTRACT

To improve the signal-to-noise ratio in trace analysis in gases or plasmas (3) by absorption spectroscopy the wavelength of the analyzing beam of a semiconductor laser (1) is modulated by a frequency $f_1$ and the absorption length or population density of absorbing particles of the plasma is modulated by a frequency $f_2$. For the measurement a lock-in amplifier (5) coupled to a photodiode (4) is tuned to the sum or difference frequency of the frequencies $f_1$ and $f_2$ or whole-number multiples thereof.

13 Claims, 1 Drawing Sheet

SPECTROSCOPIC METHOD WITH DOUBLE MODULATION

BACKGROUND OF THE INVENTION

1. Field of the Invention

The present invention relates to a method of measuring the absorption or reflection of electromagnetic radiation by a material sample for a given wavelength of electromagnetic radiation with a beam source (1) in which radiation said material sample (3) is located and a beam detector (4) for detecting the radiation transmitted or reflected by said material sample, whereby the wavelength of the beam incident on said material sample is modulated by a first frequency ($f_1$), whereby the modulated wavelength of said incident beam constitutes a first parameter, and a frequency-selective measurement is carried out phase-sensitive by at least one lock-in amplifier connected to said beam detector (4), it further relating to an apparatus for implementation thereof.

2. Description of the Prior Art

In optical spectroscopy there is often the problem of defining minimally small signals or signal changes of such optical parameters as absorption or reflection of electromagnetic radiation by a material sample. Absorption spectroscopy is one sensitive method of qualitative and quantitative analysis of trace elements in a material sample. The detection limit in absorption spectroscopy is given by the minimally detectable absorption determined by the signal-to-noise ratio. By employing modulation techniques (periodic change in characteristic parameters, such as e.g. amplitude, wavelength, etc and correlated measurement of the signal for modulation) it is possible to suppress or diminish noise signals as a function of the frequency (flicker noise). The resulting improvement in the signal-to-noise ratio produces a reduction in the detection limit.

One commonly employed technique is the periodic modulation of the wavelength of electromagnetic radiation which may be achieved, when laser diodes are used as the light sources, by periodically changing the laser diode current (see e.g. J. A. Silver, Applied Optics 31, 707 (1992) and the literature referenced therein). A laser beam modulated in such a way is passed through a material sample, e.g. a gas or plasma and is sensed by a beam detector, e.g. a photodiode in which a photocurrent is generated. The beam detector is coupled to a lock-in amplifier adjusted to the modulation frequency of the laser beam or the multiple thereof. By modulating the wavelength of the radiation of the laser diode in the kHz range it is possible to measure absorptions down to approx. $10^{-5}$ (for a detection bandwidth of 1 Hz).

The stated detection limit of $10^{-5}$ is determined by non-specific background signals caused by interference and etalon effects as well as by the amplitude modulation of the laser diode radiation, modulation of the laser diode current resulting namely not only in modulation of the wavelength but also modulation of the amplitude. The fluctuations in the stated background signals determine the signal-to-noise ratio at the detection limit.

SUMMARY OF THE INVENTION

The object of the present invention is thus to further lower the detection limit in spectroscopic measurement of minimally small absorption or reflection signals or changes thereof.

This object is achieved by a method of measuring the absorption or reflection capacity of a material sample (3) for a given wavelength of electromagnetic radiation with a beam source (1) in which radiation said material sample (3) is located and a beam detector (4) for detecting the radiation transmitted or reflected by said material sample, whereby the wavelength of the beam incident on said material sample is modulated by a first frequency ($f_1$), whereby the modulated wavelength of said incident beam constitutes a first parameter, and a frequency-selective measurement is carried out phase-sensitive by at least one lock-in amplifier connected to said beam detector (4), characterized in that a further parameter determining the amplitude of the radiation transmitted or reflected by said material sample (3) is modulated by a second frequency ($f_2$) and that either a lock-in amplifier is operated with the sum or difference frequency of said first and second frequencies ($f_1$) and ($f_2$) or whole-number multiples thereof, or that two lock-in amplifiers circuited in series, and each operated at the frequencies ($f_1$) and ($f_2$) are employed, and an apparatus for implementation thereof. Advantageous modified forms include: a method wherein the further parameter is either one of the optical properties of the material sample at the given wavelength, or the optical depth of the material sample at the given wavelength, or the absorption length of the material sample at the given wavelength, or the population density of absorbing particles; a method wherein the material sample is a gas or plasma and the further parameter is the number of particles in the absorption volume absorbing at the given wavelength, and such a method wherein the power coupled into the plasma is modulated by the second frequency ($f_2$); apparatus wherein the beam source is a semiconductor laser and wherein the device for modulating the wavelength of the radiation at a first frequency is a frequency generator for modulating the injection current of the semiconductor laser; apparatus wherein the material sample is a plasma and the device for modulating a further parameter with a second frequency is a frequency generator for modulating the power coupled into the plasma; and use of any of the aforementioned methods or apparatus for qualitative and quantitative trace analysis in gases or plasmas.

The invention has the advantage that by means of a second independent means of modulating a further parameter of the measurement system, the stated fluctuations may be overcome and a minimally detectable absorption lowered by 1–3 magnitudes. This parameter may be e.g. the absorption length in the material sample.

DETAILED DESCRIPTION OF THE INVENTION

Figure 3:
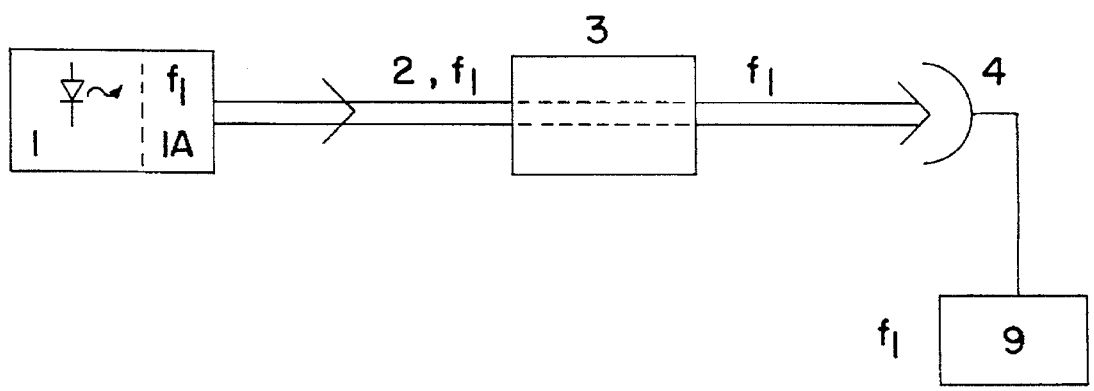
FIG. 3 schematically represents a prior art arrangement.

Referring to the drawings, and first to FIG. 3 thereof, the light source 1, preferably a semiconductor laser emits a narrow-band pencil beam 2 having a wavelength λ. The light source 1 contains a device 1A, by means of which the pencil beam 2 is modulated at a first frequency $f_1$. This device 1A is, in the case of a semiconductor laser as the light source 1, preferably a frequency generator with which the injection current of the semiconductor laser is modulated with the frequency $f_1$, this being achieved such that a current as a time function of the frequency $f_1$ is added to a DC current of constant strength. In this case both the wavelength and the amplitude of the pencil beam 2 are modulated by the frequency $f_1$. The device 1A may also be a mechanical interrupter (chopper), then only the amplitude of the pencil beam 2 can be modulated by the frequency $f_1$.

The pencil beam then passes through a material sample 3 being analyzed, the absorption of which is to be measured at the wavelength λ and is detected by a beam detector, e.g. a photodiode. The photocurrent generated by the beam detector is applied to a lock-in amplifier 9 with which a frequency-selective measurement is carried out.

When the lock-in amplifier 9 is set to the frequency $f_1$ the configuration described so far is in keeping with that of prior art, by means of which, for example, trace elements may be detected in a gas or plasma as the material sample 3.

Now, however, (and referring to FIG. 1) to improve the signal-to-noise ratio an additional modulation is introduced at a second frequency $f_2$, it being important in this respect that in addition to the wavelength or amplitude of the radiation emitted by the semiconductor laser a further parameter is found, from which the amplitude of the beam detected by the detector 4 also depends. This parameter is modulated by a frequency $f_2$ by means of a suitable device 6 to which the measurment system is coupled. The lock-in amplifier 5 is then set to the sum or difference of the two modulation frequencies $f_1$ and $f_2$ or whole number multiples thereof. Alternatively, however, as shown in FIG. 2, two-lock in amplifiers 7,8 may be circuited in series at the output of the beam detector 4, of which one is set to the frequency $f_1$ and the other to the frequency $f_2$.

Figure 1:
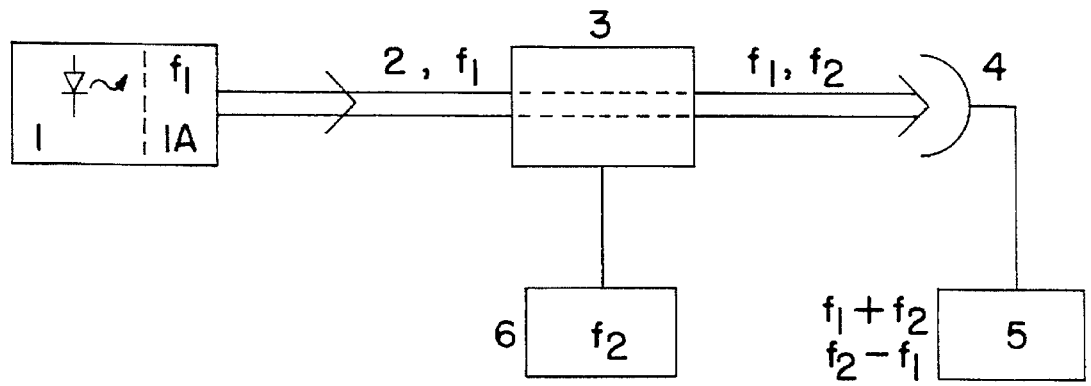
FIG. 1 schematically represents an example embodiment of the invention.
Figure 2:
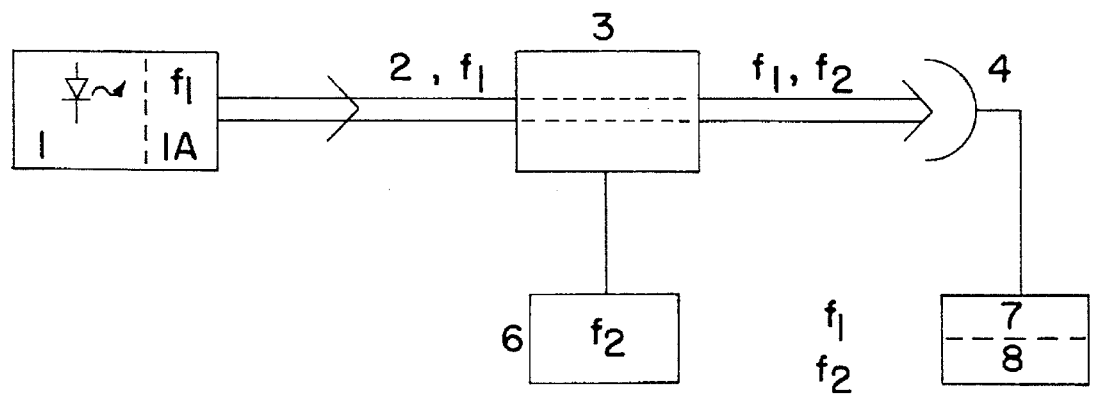
FIG. 2 schematically represents an alternative example embodiment of the invention.

In accordance with the embodiment of the present invention as shown in FIGS. 1 and 2 a property of the material sample 3 is employed as a further modulation parameter, this being preferably an optical property of the sample such as, e.g., its optical depth at the wavelength λ. The optical depth is the product of the absorption length, the number of absorbent particles (population density) and the absorption cross-section. Of these parameters the absorption length and population density in particular may be varied to especially good advantage. For instance, the population density in plasmas (current-carrying and non-current carrying) may be modulated by varying the power coupled into the system. It is often the case that a change in the absorption length is also involved in power modulation. For any absorption volume the absorption length may be modulated by changing the light path (e.g. multiple transitions, achievable by an electrically adjustable system of mirrors).

One example of that achieved by the method described is the analysis of element traces in gases. To generate free atoms and, where necessary, excited atoms in metastable states it is necessary to introduce the components to be analyzed in a plasma, e.g. a microwave plasma. The radiation of the laser diode is passed through the plasma and set to a specific absorption line of the components to be analyzed. Modulation of the emitted wavelength of the laser diode is achieved by varying the current, modulating the absorption in the absorption volume (plasma) by changing the power coupled into the plasma. The signal is detected by a photodiode and evaluated by a lock-in amplifier to the sum or difference frequency of the modulations or whole-number multiples of these frequencies.

Preferably, the modulation frequency $f_1$ is in the kHz range and the modulation frequency $f_2$ in the range of a few 100 kHz to the MHz range.

As an alternative to the embodiment shown in FIGS. 1 and 2 it is also conceivable that minimal changes in the reflectivity of a material sample 3 need to be detected. In this case the optical sample property to be modulated is the refractive index at the wavelength λ. The refractive index may also be varied, e.g. by a change in absorption at the wavelength λ or also however, by a change in absorption at other wavelengths, e.g. in accordance with the Kramers-Kronig relations applicable for semiconductors. Changing the absorption may be caused by altering the population density, as already described above.

What is claimed is:

1. A method of measuring the absorption or reflection capacity of a material sample (3) for a given wavelength of electromagnetic radiation with a beam source (1) and a beam detector (4) for detecting the radiation transmitted or reflected by said material sample, wherein said material sample is located in said radiation whereby the wavelength of the beam incident on said material sample is modulated by a first frequency ($f_1$), whereby the modulated wavelength of said incident beam constitutes a first parameter, and a frequency-selective measurement is carried out phase-sensitive by at least one lock-in amplifier connected to said beam detector (4), characterized in that a further parameter determining the amplitude of the radiation transmitted or reflect ed by said material sample (3) is modulated by a second frequency ($f_2$) and that either a lock-in amplifier is operated with the sum or difference frequency of said first and second frequencies ($f_1$) and ($f_2$) or whole-number multiples thereof, or that two lock-in amplifiers circuited in series, and each operated at the frequencies ($f_1$) and ($f_2$) are employed.

2. The method as set forth in claim 1, characterized in that said further parameter is one of the optical properties of said material sample (3) at said given wavelength.

3. The method as set forth in claim 2, characterized in that said further parameter is the optical depth of said material sample (3) at said given wavelength.

4. The method as set forth in claim 3, characterized in that said further parameter is the absorption length of said material sample (3) at said given wavelength.

5. The method as set forth in claim 3, characterized that said further parameter is the population density of absorbing particles.

6. The method as set forth in any of the claims 1, 3 or 5, characterized in that said material sample (3) is a gas or plasma into which power is coupled and that said further parameter is the number of particles in the absorption volume absorbing at said given wavelength.

7. The method as set forth in claim 6, characterized in that said power coupled into the plasma is modulated by said second frequency ($f_2$).

8. The method as set forth in claim 1, wherein said material sample is selected from the group consisting of gases and plasmas, and wherein said measuring provides qualitative and quantitative trace analysis.

9. An apparatus for measuring the absorption or reflection capacity of a material sample (3) for a given wavelength of electromagnetic radiation with a beam source (1) in the beam of which said material sample (3) is located, a device (1A) for modulating the wavelength of the radiation at a first frequency ($f_1$), whereby the modulated wavelength of said radiation constitutes a first parameter, a beam detector (4) and at least one lock-in amplifier coupled to said beam detector (4) for frequency-selective measurement, characterized in that the measurement system is coupled to a device (6) for modulating a further parameter with a second frequency ($f_2$), and that said lock-in amplifier coupled to said beam detector (4) is set to the sum or difference frequency of said first and second frequencies ($f_1$) and ($f_2$) or whole-number multiples thereof, or that two lock-in amplifiers circuited in series with said beam detector (4) are each set to said first and second frequencies ($f_1$) and ($f_2$).

10. The apparatus as set forth in claim 9, characterized in that said beam source (1) is a semiconductor laser.

11. The apparatus as set forth in claim 10, characterized in that said device (1A) for modulating the wavelength of the radiation at a first frequency is a frequency generator for modulating the injection current of said semiconductor laser.

12. The apparatus as set forth in claim 9, characterized in that said material sample (3) is a plasma into which power is coupled and that said device (6) for modulating a further parameter with a second frequency ($f_2$) is a frequency generator for modulating said power coupled into said plasma.

13. That method of using apparatus as set forth in claim 9, wherein said material sample is selected from the group consisting of gases and plasmas, and wherein said measuring provides qualitative and quantitative trace analysis.

* * * * *